United States Patent [19]

Olefsky

[11] Patent Number: 5,708,012
[45] Date of Patent: Jan. 13, 1998

[54] USE OF THIAZOLIDINEDIONE DERIVATIVES AND RELATED ANTIHYPERGLYCEMIC AGENTS IN THE TREATMENT OF INSULIN RESISTANT SUBJECTS WITH NORMAL GLUCOSE TOLERANCE IN ORDER TO PREVENT OR DELAY THE ONSET OF NONINSULIN-DEPENDENT MELLITUS

[75] Inventor: Jerrold M. Olefsky, Solana Beach, Calif.

[73] Assignee: Sankyo Company, Limited, Tokyo, Japan

[21] Appl. No.: 431,266

[22] Filed: Apr. 28, 1995

[51] Int. Cl.$^6$ ..................................... A01N 43/40
[52] U.S. Cl. .................. 514/337; 514/359; 514/369; 514/370; 514/439; 514/443; 514/444; 514/455; 514/456
[58] Field of Search .................. 514/337, 359, 514/369, 370, 439, 443, 444, 455, 456

[56] References Cited

U.S. PATENT DOCUMENTS

| | | |
|---|---|---|
| 4,287,200 | 9/1981 | Kawamatsu et al. |
| 4,340,605 | 7/1982 | Kawamatsu et al. |
| 4,438,141 | 3/1984 | Kawamatsu et al. |
| 4,444,779 | 4/1984 | Kawamatsu et al. |
| 4,461,902 | 7/1984 | Kawamatsu et al. |
| 4,572,912 | 2/1986 | Yoshioka et al. |
| 4,687,777 | 8/1987 | Meguro et al. |
| 4,703,052 | 10/1987 | Eggler et al. |
| 4,725,610 | 2/1988 | Meguro et al. |
| 4,873,255 | 10/1989 | Yoshioka et al. |
| 4,897,393 | 1/1990 | Iijima et al. |
| 4,897,405 | 1/1990 | Alessi et al. |
| 4,918,091 | 4/1990 | Cantello et al. |
| 4,948,900 | 8/1990 | Iijima et al. |
| 5,002,953 | 3/1991 | Hindley . |
| 5,061,717 | 10/1991 | Clark et al. |
| 5,120,754 | 6/1992 | Clark et al. |
| 5,132,317 | 7/1992 | Cantello et al. |
| 5,194,443 | 3/1993 | Hindley . |
| 5,223,522 | 6/1993 | Clark et al. .......... 514/369 |
| 5,232,925 | 8/1993 | Hindley . |
| 5,260,445 | 11/1993 | Hindley . |

FOREIGN PATENT DOCUMENTS

| | | |
|---|---|---|
| 4-69383 | 3/1992 | Japan . |
| WO 89/08651 | 9/1989 | WIPO . |
| WO 91/07107 | 5/1991 | WIPO . |
| WO 92/02520 | 2/1992 | WIPO . |
| WO 94/01433 | 1/1994 | WIPO . |

*Primary Examiner*—John M. Cooney, Jr.
*Attorney, Agent, or Firm*—Frishauf, Holtz, Goodman, Langer & Chick, P.C.

[57] ABSTRACT

Novel methods of using thiazolidinone derivatives and related antihyperglycemic agents to treat populations exhibiting insulin resistent non-impaired glucose tolerance (IRNIGT) in order to prevent or delay the onset of noninsulin-dependent diabetes mellitus (NIDDM) and complications arising therefrom are disclosed.

26 Claims, No Drawings

USE OF THIAZOLIDINEDIONE DERIVATIVES AND RELATED ANTIHYPERGLYCEMIC AGENTS IN THE TREATMENT OF INSULIN RESISTANT SUBJECTS WITH NORMAL GLUCOSE TOLERANCE IN ORDER TO PREVENT OR DELAY THE ONSET OF NONINSULIN-DEPENDENT MELLITUS

FIELD OF THE INVENTION

The present invention is a method using thiazolidinedione compounds for the treatment of non-diabetic insulin resistant patients who do not have impaired glucose (IGT). Upon oral glucose tolerance testing, these subjects will have normal glucose tolerance by World Health Organization criteria and treatment with thiazolidinedione compounds may prevent or delay the onset of noninsulin-dependent diabetes mellitus (NIDDM). More specifically, the present invention involves, in one embodiment, administering certain known thiazolidinedione compounds and related antihyperglycemic agents which increase glucose tolerance, to an individual, who is neither in the state of NIDDM, nor in the state of impaired glucose tolerance (IGT) but who is insulin resistant with NGT as define herein, thus preventing or delaying the onset of NIDDM or complications resulting therefrom. Since this subject group is insulin resistant, but does not have IGT, they will be referred to herein as non-IGT (NIGT) or insulin resistant non-IGT (IRNIGT).

BACKGROUND

Insulin resistance is a classic feature of many human conditions, such as NIDDM (non-insulin dependent diabetes mellitus), obesity, hypertension, aging, etc.

Perhaps the most well-studied of these situations is NIDDM. Diabetes is one of the most prevalent chronic worldwide with significant personal and financial costs patients and their families, as well as for society. Different types of diabetes exist with distinct etiologies and pathogeneses.

Diabetes mellitus is a disorder of carbohydrate metabolism, characterized by hyperglycemia and glycosuria and resulting from inadequate production or utilization of insulin.

NIDDM (sometimes otherwise referred to as Type II diabetes) is a form of diabetes where utilization of insulin is inadequate.

NIDDM occurs predominantly in adults in whom adequate production of insulin is available for use, yet a defect exists in insulin-mediated utilization and metabolism of glucose in peripheral tissues. It has been shown that for some people with diabetes a genetic predisposition results in a mutation in the gene(s) coding for insulin and/or the insulin receptor and/or insulin-mediated signal transduction factor(s), thereby resulting in ineffective insulin and/or insulin-mediated effects thus impairing the utilization or metabolism of glucose.

Diabetes mellitus often develops from certain at risk populations; it is known that one such population is individuals with impaired glucose tolerance (IGT). The usual meaning of impaired glucose tolerance is that it is a condition intermediate between frank, noninsulin-dependent diabetes mellitus and normal glucose tolerance. IGT is diagnosed by a procedure wherein an affected person's postprandial glucose response is determined to be abnormal as assessed by 2-hour postprandial plasma glucose levels. In this test, a measured amount of glucose is given to the patient and blood glucose levels measured regular intervals, usually every half hour for the first two hours and every hour thereafter. In a "normal" or non-IGT individual glucose levels rise during the first two hours to level less than 140 mg/dl and then drop rapidly. In an impaired individual (IGT) the blood glucose levels are higher and the drop-off level is at a slower rate. A high percentage of the impaired (IGT) population is known to progress to noninsulin-dependent diabetes mellitus (NIDDM).

The present invention is based on the discovery that a certain population that tests normal according to the fasting and two hour postprandial test measurement (i.e. normal glucose tolerance population) but shows insulin resistance using different tests, also progresses to NIDDM, and that this population can be treated with thiazolidinedione compounds. The population which tests as having normal glucose tolerance by the usual oral glucose tolerance test (NGT) but tests as having insulin resistance is designated herein as having non-IGT (NIGT) or insulin resistant non-IGT.

It is important to distinguish individuals whose tests show normal glucose tolerance and who are not insulin resistant on the one hand, and who are of normal glucose tolerance but who have a certain degree of insulin resistance on the other hand.

Insulin resistance is an abnormality of glucose disposal in tissues and organs which can be measured, for example, by the euglycemic glucose clamp test. Alternatively, it can be measured by the intravenous glucose tolerance test, or in the simplest way by measuring the fasting insulin level. It is well known that there is an excellent correlation between the height of the fasting insulin level and the degree of insulin resistance. Therefore, one could use elevated fasting insulin levels as a surrogate marker for insulin resistance for the purpose of identifying which NGT individuals have insulin resistance.

Another way to do this is to follow the approach as disclosed in The New England Journal of Medicine, No. 3, pp. 1188 (1994), i.e. to select obese subjects as an initial criteria for entry into the treatment group. Some obese subjects have impaired glucose tolerance (IGT) while others have normal glucose tolerance (NGT). Since essentially all obese subjects are insulin resistant, i.e. even the NGT obese subjects are insulin resistant, they have fasting hyperinsulinemia. Therefore, the target of the treatment according to the present invention can be defined as NGT individuals who are obese or who have fasting hyperinsulinemia, or who have both.

The euglycemic clamp test involves the simultaneous administration of a constant insulin infusion and a variable rate glucose infusion. During the test, which lasts 3–4 hours, the plasma glucose concentration is kept constant at euglycemic levels by measuring the glucose level every 5–10 minutes and then adjusting the variable rate glucose infusion to keep the plasma glucose level unchanged. Under these circumstances, the rate of glucose entry into the bloodstream is equal to the overall rate of glucose disposal in the body. The difference between the rate of glucose disposal in the basal state (no insulin infusion) and the insulin infused state, represents insulin mediated glucose uptake. In normal individuals, insulin causes brisk and large increase in overall body glucose disposal, whereas in NIDDM subjects, this effect of insulin is greatly blunted, and is only 20–30% of normal. In insulin resistant subjects with either IGT or NGT, the rate of insulin stimulated glucose disposal is about half way between normal and NIDDM. For example, at a steady state plasma insulin concentration of about 100 uU/ml (a physiological level) the glucose disposal rate in normal subjects is about 7 mg/kg/min. In NIDDM subjects, it is about 2.5 mg/kg/min, and in patients with IGT (or insulin resistant subjects with NGT) it s about 4–5 mg/kg/min. This is a highly reproducible and precise test, and can distinguish patients within these categories. It is also known, that as subjects become more insulin resistant, the fasting insulin level rises. There is an excellent positive correlation between the height of the fasting insulin level and the magnitude of the insulin resistance as measured by euglycemic glucose clamp tests and, therefore, this provide the rationale for using fasting insulin levels as a surrogate measure of insulin resistance.

DESCRIPTION OF THE INVENTION

The present invention provides a method fog the treatment of IRNIGT in order to prevent or delay the onset of NIDDM. It is known that persons with impaired glucose tolerance have a much higher rate of progression to NIDDM than persons with normal glucose tolerance. Saad, et al., *New Engl J Med* 1988; 319:1500–6. However, as noted above, IRNIGT can also progress to NIDDM. If the insulin resistance can be normalized, the progression to NIDDM can be delayed or prevent.

The importance of delaying or preventing NIDDM cannot be over-emphasized. Untreated NIDDM can result in mortality due to cardiovascular disease and in other diabetic complications including retinopathy, nephropathy, and peripheral neuropathy.

Therefore, it is one object of the invention to provide a method of treating insulin resistant populations with NIGT in order to prevent or delay the onset of NIDDM thereby, bringing relief of symptoms, improving the quality of life, preventing acute and long-term complications, reducing mortality and treating accompanying disorders of those at risk for NIDDM. This object is met by a method of using the disclosed compounds for treating insulin resistant populations exhibiting NIGT to prevent or delay the onset of NIDDM as taught herein.

Patients with insulin resistance, who have NGT are also hyperinsulinemic, and have a number of other metabolic abnormalities such as hypertriglyceridemia, low HDL levels, increased incidence of hypertension, and increase, risk of atherosclerosis. This cluster of abnormalities is commonly called the "Metabolic Syndrome", or "the Insulin Resistance Syndrome", or "Syndrome X". Even beyond the prevention of NIDDM, an effective treatment of insulin resistance in this category of subjects would also reverse many of the metabolic, abnormalities associated with this syndrome. Thereby, an effective treatment of insulin resistance could also lower the risk for the complications of atherosclerosis.

DETAILED DESCRIPTION

Compounds useful for practicing the present invention, and methods of making these compounds are known. Some of these compounds are disclosed in WO 91/07107; WO 92/02520; WO 94/01433; WO 89/08651; JP Kokai 69383/92; U.S. Pat. Nos. 4,287,200; 4,340,605; 4,438,141; 4,444,779; 4,461,902; 4,572,912; 4,687,777; 4,703,052; 4,725,610; 4,873,255; 4,897,393; 4,897,405; 4,918,091; 4,948,900; 5,002,953; 5,061,717; 5,120,754; 5,132,317; 5,194,443; 5,223,522; 5,232,925; and 5,260,445. The active compounds disclosed in these publications are useful as therapeutic agents for the treatment of diabetes hyperglycemia, hypercholesterolemia, and hyperlipidemia. The disclosure of these publications are incorporated herein by reference in particular with respect to the active compounds disclosed therein, and methods of preparation thereof. These compounds are useful for the treatment of insulin resistance in patients with NIGT (i.e. IRNIGT) in order to prevent or delay onset of NIDDM and complications resulting therefrom, in accordance with the present invention.

There is no disclosure in the above-identified publications to use the compounds identified in this present application in the treatment of insulin resistant populations in order to prevent or delay the onset of NIDDM and complications resulting therefrom. Insulin resistance with NIGT (i.e. IRNIGT) is not the same as NIDDM. Nor is the host to which the treatment is being applied, the same. A person with insulin resistance and NIGT does not have NIDDM.

It is believed by the inventor hereof that insulin resistance is a common feature of NIDDM, IGT and IRNIGT and that thiazolidinedione compounds improve insulin resistance of all three states mentioned. However, this does not lead to the conclusion that amelioration of IGT and IRNIGT by virtue of improvement of insulin resistance by the administration of a thiazolidinedione compound is obvious in view of the prior knowledge that NIDDM is ameliorated by virtue of improvement of insulin resistance by the administration of thiazolidinedione compounds. This can be seen from the following:

It is well established that the insulin resistance in NIDDM is composed of two separate components: a primary component and a secondary component.

The primary component consists of the genetic contribution to insulin resistance which exists in the prediabetic state. This leads to hyperinsulinemia which, if sustained, compensates for the insulin resistance, preventing the onset of diabetes. Once β-cell insulin secretion begins to fail, hyperglycemia occurs, leading to the clinical state of diabetes. After the hyperglycemic diabetic state emerges, the insulin resistance gets worse, and this worsening comprises the secondary component of insulin resistance. Thus, in NIDDM there exists the primary inherited component and the secondary, acquired component of insulin resistance, and these two distinct components are about equal in magnitude. In IGT, no secondary component exists at all.

The fact that insulin resistance consists of a primary and secondary component, and that it worsens as one goes from prediabetes to NIDDM is known inter alia from the following reported findings:

(i) The magnitude of insulin resistance as measured by euglycemic glucose clamp tests, or other methods, is greater in patients with NIDDM than in those patients with IGT or in prediabetic patients who do not have IGT.

(ii) When offspring of NIDDM patients were studied, all of them were insulin resistant. However, the offspring who had already developed NIDDM were more insulin resistant than their non-diabetic siblings. Diabetic and non-diabetic offspring were matched for age, body mass index, diet, and other variables, and so the factor responsible for the greater insulin resistance in the NIDDM offspring was the presence of NIDDM itself.

(iii) When identical twins discordant for NIDDM were studied, it was found that both twins were insulin resistant, but that the diabetic twin was more insulin resistant than the non-diabetic twin. Obviously, the twin pairs are completely matched for genetic load, obesity, etc., and the only difference is the presence or absence of NIDDM. Therefore, this provides the best evidence for the conclusion that insulin resistance worsens when NIDDM develops, leading to the concept of a primary and secondary component.

Referring to the concept discussed above, it is now well described that hyperglycemia, per se, will cause insulin resistance. This has been demonstrated in vitro, where it is commonly found that incubation of cells under hyperglycemic conditions leads to decreased insulin receptor function. This is similar to the decreased insulin receptor kinase activity seen in NIDDM patients. When animals are made experimentally hyperglycemic, they become insulin resistant, and when the hyperglycemia is removed, the insulin resistance goes away. When humans are made experimentally hyperglycemic, they also become insulin resistant. All of these findings lead to the conclusion that hyperglycemia will cause a secondary state of insulin resistance which, in NIDDM, is superimposed on the primary genetic abnormality and this secondary component is not present in IGT.

The above conclusions are consistent with the findings reported by J. A. Scarlet et al and by W. T. Garvey et al. Scarlet et al treated NIDDM patients with exogenous insulin and concluded that the post receptor defect in insulin-stimulated glucose disposal is substantially ameliorated by exogenous insulin treatment suggesting that this component of the defect in insulin action is an acquired abnormality which is secondary to some aspect of the hyperglycemic, insulin-deficient state ["Insulin treatment reverses the insulin resistance of Type II diabetes mellitus", Diabetes Care, 5 (4), p. 353, 1982]. Garvey et al conducted intensive insulin therapy on NIDDM patients and reported that diabetic subjects maintain lower glucose values concomitant with (i) partial reversal of the insulin resistance, (ii) near-normalization of basal hepatic glucose output, and (iii) enhanced insulin secretory responses ["The effect of insulin treatment on insulin secretion and insulin action in Type II diabetes mellitus", Diabetes, 39, March, p. 222, 1985]. These reports lead to the conclusion that intensive insulin management normalizes the hyperglycemia in NIDDM, which then reverses the secondary component of insulin resistance. After the hyperglycemia is normalized, since only the secondary component of insulin resistance is reversed, patients will remain insulin resistant (but less so than in the hyperglycemic state), and their insulin resistance is comparable to that which exists in IGT. Thus, in treated NIDDM patients, the primary component of insulin resistance is the main residual abnormality.

Although we know that thiazolidinediones can ameliorate insulin resistance, there is in vitro data which suggests that the effect of thiazolidinediones is to improve the secondary, or hyperglycemia-induced, component of insulin resistance. Thus, Kellerer et al, "Troglitazone Prevents Glucose-Induced Insulin Resistance of Insulin Receptor in Rat 1 Fibroblasts", *Diabetes*, 43:447–453 (1994), showed that when cells are incubated under hyperglycemic conditions in vitro, they show a decease in insulin receptor kinase activity and become insulin resistant. When cells were treated with thiazolidinediones and hyperglycemic conditions, the effect of the hyperglycemia to cause cellular insulin resistance was prevented. From these results, combined with the earlier cited findings, it is reasonable to conclude that when thiazolidinediones are given to NIDDM patients, and insulin resistance is partially ameliorated, it is the secondary component of insulin resistance which is favorably affected and not the primary component. Since patients with IRNIGT only have the primary component of insulin resistance, and do not have the secondary component, it also follows that thiazolidinediones would not necessarily be effective in these patients.

It is known that treatment of hyperglycemic NIDDM patients with certain thiazolidinedione compounds, e.g. Troglitazone, partially reverses the insulin resistance [S. L. Suter et al, "Metabolic effects of a new oral hypoglycemic agent, CS-045, in non-insulin dependent diabetic subjects" Diabetes Care, 15 (2), p. 193, 1992]. The effect of the drug improved the insulin resistance of NIDDM about 40% of the way towards normal. Thus, after the drug treatment, the patients were still insulin resistant, and the magnitude of this residual insulin resistance was comparable to the magnitude of insulin resistance in IGT or IRNIGT.

The findings from treatment of NIDDM with exogenous insulin or with thiazolidinediones, when considered together with some of the above-mentioned results, leads to the interpretation that thiazolidinediones are effective at treating the secondary component of insulin resistance. Since this secondary component of insulin resistance exists only in NIDDM patients, and is not present in IRNIGT, one is led to the conclusion that thiazolidinediones such as Troglitazone would not improve insulin resistance in IRNIGT individuals since they have only the primary component of insulin resistance.

SUMMARY OF THE INVENTION

The present invention provides a method for the treatment of nondiabetic insulin resistant patients with non-impaired glucose tolerance (IRNIGT) in order to prevent or delay the onset of NIDDM. It has been determined that persons with IRNIGT have a much higher rate of progression to NIDDM than normal individuals. If IRNIGT can be normalized, the progression to NIDDM could be delayed or prevented in this population.

Compounds useful for practicing the present invention reduce fasting insulin levels, improve insulin sensitivity, and improve glucose tolerance in many individuals. As agents having the aforementioned effects (in the improvement of glucose tolerance), the compounds of the formulas I–XIII are useful in prophylactically treating individuals to prevent or delay the onset of NIDDM.

DETAILED DESCRIPTION OF THE INVENTION

Accordingly, the present invention is the use of compounds of Formula I

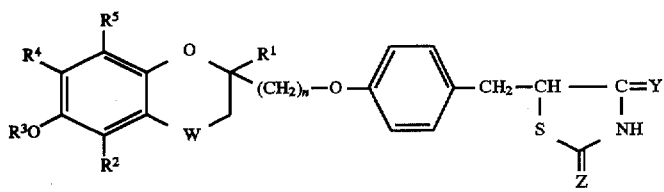

I wherein $R^1$ and $R^2$ are the same or different and each represents a hydrogen atom or a $C_1$–$C_5$ alkyl group;

$R^3$ represents a hydrogen atom, a $C_1$–$C_6$ aliphatic acyl group, an alicyclic acyl group, an aromatic acyl group, a heterocyclic acyl group, an araliphatic acyl group, a ($C_1$–$C_6$ alkoxy)carbonyl group, or an aralkyloxycarbonyl group;

$R^4$ and $R^5$ are the same or different and each represents a hydrogen atom, a $C_1$–$C_5$ alkyl group or a $C_1$–$C_5$ alkoxy group, or $R^4$ and $R^5$ together represent a $C_1$–$C_4$ alkylenedioxy group;

n is 1, 2, or 3;

W represents the —$CH_2$—, >CO, or CH—$OR^6$ group (in which $R^6$ represents any one of the atoms or groups defined for $R^3$ and may be the same as or different from $R^3$); and Y and Z are the same or different and each represents an oxygen atom or an imino (=NH) group;

and pharmaceutically acceptable salts thereof.

The present invention is also the use of compounds of the Formula II

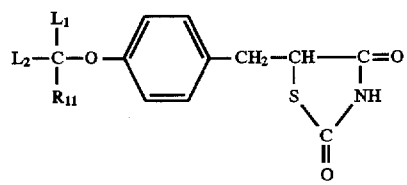

II wherein $R_{11}$ is substituted or unsubstituted alkyl, alkoxy, cycloalkyl, phenylalkyl, phenyl, aromatic acyl group, a 5- or 6-membered heterocyclic group including 1 or 2 heteroatoms selected from the group consisting of nitrogen, oxygen, and sulfur, or a group of the formula

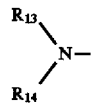

wherein $R_{13}$ and $R_{14}$ are the same or different and each is lower alkyl or $R_{13}$ and $R_{14}$ are combined to each other either directly or as interrupted by a heteroatom selected from the group consisting of nitrogen, oxygen, and sulfur to form a 5- or 6-membered ring; wherein $R_{12}$ means a bond or a lower alkylene group; and wherein $L_1$ and $L_2$ are the same or different and each is hydrogen or lower alkyl or $L_1$ and $L_2$ are combined to form an alkylene group; or a pharmaceutically acceptable salt thereof.

The present invention is also the use of compounds of the Formula III

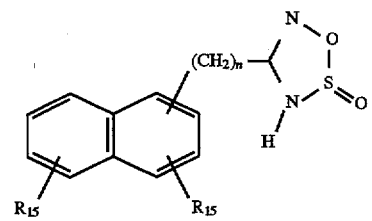

III wherein $R_{15}$ and $R_{16}$ are independently hydrogen, lower alkyl containing 1 to 6 carbon atoms, alkoxy containing 1 to 6 carbon atoms, halogen, ethynyl, nitrile, methylthio, trifluoromethyl, vinyl, nitro, or halogen substituted benzyloxy; n is 0 to 4 and the pharmaceutically acceptable salts thereof.

The present invention is also directed to the use of compounds of the Formula IV

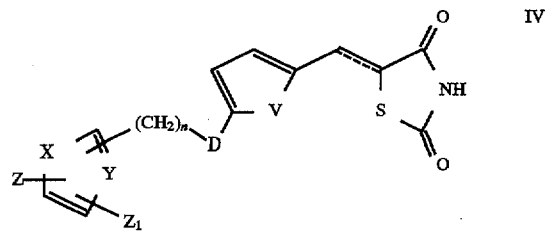

IV wherein the dotted line represents a bond or no bond;

V is —CH=CH—, —N=CH—, —CH=N— or S;

D is $CH_2$, CHOH, CO, C=$NOR_{17}$ or CH=CH;

X is S, O, $NR_{18}$, —CH=N or —N=CH;

Y is CH or N;

Z is hydrogen, ($C_1$–$C_7$) alkyl, ($C_3$–$C_7$)cycloalkyl, phenyl, naphthyl, pyridyl, furyl, thienyl, or phenyl mono- or disubstituted with the same or different groups which are ($C_1$–$C_3$)alkyl, trifluoromethyl, ($C_1$–$C_3$)alkoxy, fluoro, chloro, or bromo;

$Z_1$ is hydrogen or ($C_1$–$C_3$)alkyl;

$R_{17}$ and $R_{18}$ are each independently hydrogen or methyl; and n is 1, 2, or 3;

the pharmaceutically acceptable cationic salts thereof; and the pharmaceutically acceptable acid addition salts thereof when the compound contains a basic nitrogen.

The present invention is also directed to the use of compounds of the Formula V

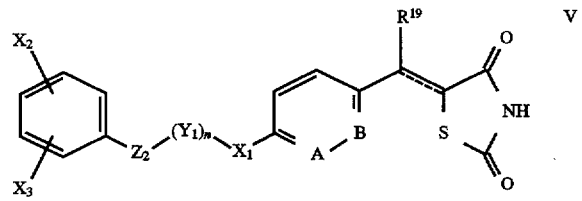

V wherein the dotted line represents a bond or no bond;

A and B are each independently CH or N, with the proviso that when A or B is N, the other is CH;

$X_1$ is S, SO, $SO_2$, $CH_2$, CHOH, or CO;

n is 0 or 1;

$Y_1$ is $CHR_{20}$ or $R_{21}$, with the proviso that when n is 1 and $Y_1$ is $NR_{21}$, $X_1$ is $SO_2$ or CO;

$Z_2$ is $CHR_{22}$, $CH_2CH_2$, CH=CH,

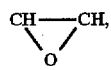

$OCH_2$, $SCH_2$, $SOCH_2$ or $SO_2CH_2$;

$R_{19}$, $R_{20}$, $R_{21}$, and $R_{22}$ are each independently hydrogen or methyl; and $X_2$ and $X_3$ are each independently hydrogen, methyl, trifluoromethyl, phenyl, benzyl, hydroxy, methoxy, phenoxy, benzyloxy, bromo, chloro, or fluoro;

a pharmaceutically acceptable cationic salt thereof; or a pharmaceutically acceptable acid addition salt thereof when A or B is N.

The present invention also relates to the use of compounds of the Formula VI

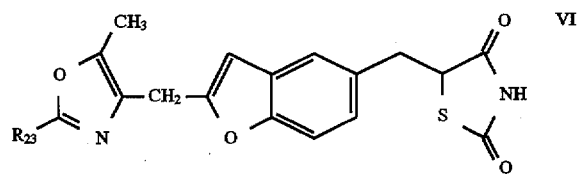

or a pharmaceutically acceptable salt thereof wherein $R_{23}$ is alkyl of 1 to 6 carbon atoms, cycloalkyl of 3 to 7 carbon atoms, phenyl or mono- or di-substituted phenyl wherein said substituents are independently alkyl of 1 to 6 carbon atoms, alkoxy of 1 to 3 carbon atoms, halogen, or trifluoromethyl.

The present invention also provides the use of a compound of Formula VII

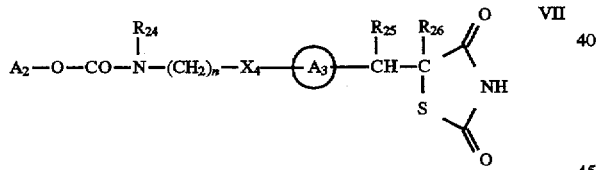

or a tautomeric form thereof and/or a pharmaceutically acceptable salt thereof, and/or a pharmaceutically acceptable solvate thereof, wherein:

$A_2$ represents an alkyl group, a substituted or unsubstituted aryl group, or an aralkyl group wherein the alkylene or the aryl moiety may be substituted or unsubstituted;

$A_3$ represents a benzene ring having in total up to 3 optional substituents;

$R_{24}$ represents a hydrogen atom, an alkyl group, an acyl group, an aralkyl group wherein the alkyl or the aryl moiety may be substituted or unsubstituted, or a substituted or unsubstituted aryl group; or $A_2$ together with $R_{24}$ represents substituted or unsubstituted $C_{2-3}$ polymethylene group, optional substituents for the polymethylene group being selected from alkyl or aryl or adjacent substituents together with the methylene carbon atoms to which they are attached form a substituted or unsubstituted phenylene group;

$R_{25}$ and $R_{26}$ each represent hydrogen, or $R_{25}$ and $R_{26}$ together represent a bond;

$X_4$ represents O or S; and n represents an integer in the range of from 2 to 6.

The present invention also provides the use of a compound of Formula VIII

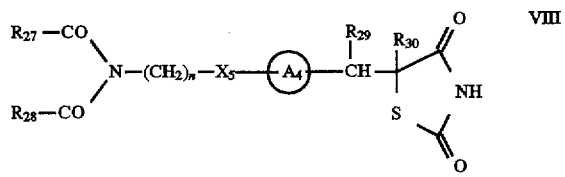

or a tautomeric form thereof and/or a pharmaceutically acceptable salt thereof, and/or a pharmaceutically acceptable solvate therefor, wherein:

$R_{27}$ and $R_{28}$ each independently represent an alkyl group, a substituted or unsubstituted aryl group, or an aralkyl group being substituted or unsubstituted in the aryl or alkyl moiety; or $R_{27}$ together with $R_{28}$ represents a linking group, the linking group consisting of an optionally substituted methylene group and either a further optionally substituted methylene group or an O or S atom, optional substituents for the said methylene groups being selected from alkyl-, aryl, or aralkyl, or substituents of adjacent methylene groups together with the carbon atoms to which they are attached form a substituted or unsubstituted phenylene group;

$R_{29}$ and $R_{30}$ each represent hydrogen, or $R_{29}$ and $R_{30}$ together represent a bond;

$A_4$ represents a benzene ring having in total up to 3 optional substituents;

$X_5$ represents O or S; and n represents an integer in the range of from 2 to 6.

The present invention also provides the use of a compound of Formula IX

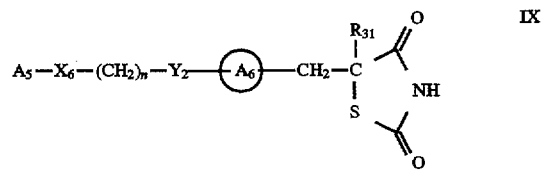

or a tautomeric form thereof and/or a pharmaceutically acceptable salt thereof, and/or a pharmaceutically acceptable solvate thereof, wherein:

$A_5$ represents a substituted or unsubstituted aromatic heterocyclyl group;

$A_6$ represents a benzene ring having in total up to 5 substituents;

$X_6$ represents O, S, or $NR_{32}$ wherein $R_{32}$ represents a hydrogen atom, an alkyl group, an acyl group, an aralkyl group, wherein the aryl moiety may be substituted or unsubstituted, or a substituted or unsubstituted aryl group;

$Y_2$ represents O or S;

$R_{31}$ represents an alkyl, aralkyl, or aryl group; and n represents an integer in the range of from 2 to 6.

Suitable aromatic heterocyclyl groups include substituted or unsubstituted, single or fused ring aromatic heterocyclyl groups comprising up to 4 hetero atoms in each ring selected from oxygen, sulphur, or nitrogen.

Favored aromatic heterocyclyl groups include substituted or unsubstituted single ring aromatic heterocyclyl groups having 4 to 7 ring atoms, preferably 5 or 6 ring atoms.

In particular, the aromatic heterocyclyl group comprises 1, 2, or 3 heteroatoms, especially 1 or 2, selected from oxygen, sulphur, or nitrogen.

Suitable values for $A_5$ when it represents a 5-membered aromatic heterocyclyl group include thiazolyl and oxazoyl, especially oxazoyl.

Suitable values for $A_5$ when it represents a 6-membered aromatic heterocyclyl group include pyridyl or pyrimidinyl.

Suitable $R_{31}$ represents an alkyl group, in particular a $C_{1-6}$ alkyl group, for example a methyl group. Preferably, $A_5$ represents a moiety of formula (a), (b), or (c):

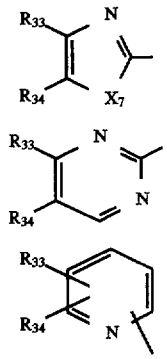

wherein:

$R_{33}$ and $R_{34}$ each independently represents a hydrogen atom, an alkyl group, or a substituted or unsubstituted aryl group or when $R_{33}$ and $R_{34}$ are each attached to adjacent carbon atoms, then $R_{33}$ and $R_{34}$ together with the carbon atoms to which they are attached form a benzene ring wherein each carbon atom represented by $R_{33}$ and $R_{34}$ together may be substituted or unsubstituted; and in the moiety of Formula (a), $X_7$ represents oxygen or sulphur.

In one favored aspect $R_{33}$ and $R_{34}$ together represent a moiety of Formula (d):

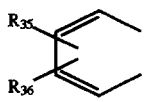

wherein $R_{35}$ and $R_{38}$ each independently represent hydrogen, halogen, substituted or unsubstituted alkyl, or alkoxy.

The present invention also provides for the use of compounds for Formula X

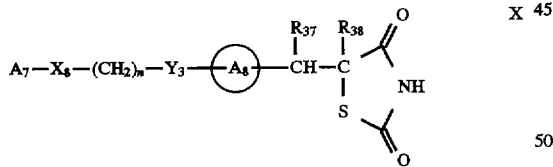

or a tautomeric form thereof and/or a pharmaceutically acceptable salt thereof, and/or a pharmaceutically acceptable solvate thereof, wherein:

$A_7$ represents a substituted or unsubstituted aryl group;

$A_8$ represents a benzene ring having in total up to 5 substituents;

$X_8$ represents O, S, or $NR_{39}$ wherein $R_{39}$ represents a hydrogen atom, an alkyl group, an acyl group, an aralkyl group, wherein the aryl moiety may be substituted or unsubstituted, or a substituted or unsubstituted aryl group;

$Y_3$ represents O or S;

$R_{37}$ represents hydrogen;

$R_{38}$ represents hydrogen or an alkyl, aralkyl, or aryl group or $R_{37}$ together with $R_{38}$ represents a bond; and n represents an integer in the range of from 2 to 6.

The present invention is also directed to the use of compounds of the Formula

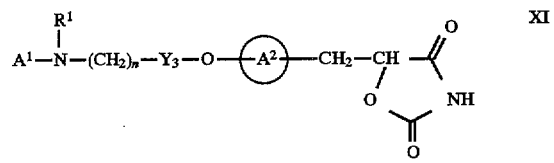

or a tautomeric form thereof and/or a pharmaceutically acceptable salt thereof, and/or a pharmaceutically acceptable solvate thereof, wherein:

$A^1$ represents a substituted or unsubstituted aromatic heterocyclyl group;

$R^1$ represents a hydrogen atom, an alkyl group, an acyl group, an aralkyl group, wherein the aryl moiety may be substituted or unsubstituted, or a substituted or unsubstituted aryl group;

$A^2$ represents a benzene ring having in total up to five substituents; and n represents an integer in the range of from 2 to 6.

Suitable aromatic heterocyclyl groups include substituted or unsubstituted, single or fused ring aromatic heterocyclyl groups comprising up to 4 hereto atoms in each ring selected from oxygen, sulphur or nitrogen.

Favoured aromatic heterocyclyl groups include substituted or unsubstituted single ring aromatic heterocyclyl groups having 4 to 7 ring atoms, preferably 5 or 6 ring atoms.

In particular, the aromatic heterocyclyl group comprises 1, 2 or 3 heteroatoms, especially 1 or 2, selected from oxygen, sulphur or nitrogen.

Suitable values for $A^1$ when it represents 5-membered aromatic heterocyclyl group include thiazolyl and oxazolyl, especially oxazolyl.

Suitable values for $A^1$ when it represents a 6-membered aromatic heterocyclyl group include pyridyl or pyrimidinyl.

Preferably, $A^1$ represents a moiety of formula (a), (b) or (c):

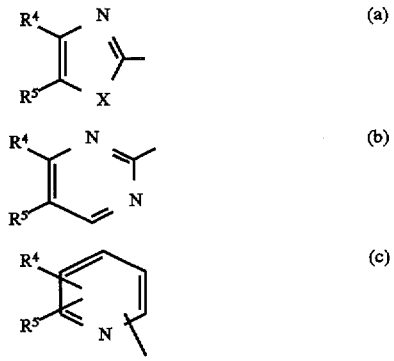

wherein:

$R^4$ and $R^5$ each independently represents a hydrogen atom, an alkyl group or a substituted or unsubstituted aryl group or when $R^4$ and $R^5$ are each attached to adjacent carbon atoms, then $R^4$ and $R^5$ together with the carbon atoms to which they are attached form a benzene ring wherein each carbon atom represented by $R^4$ and $R^5$ together may be substituted or unsubstituted; and in the moiety of formula (a)

X represents oxygen or sulphur.

The present invention is also directed to the use of compounds of the Formulas

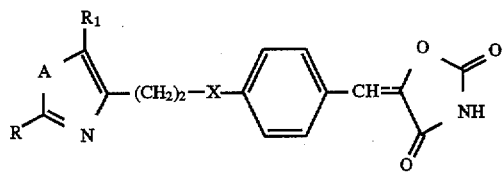

XII

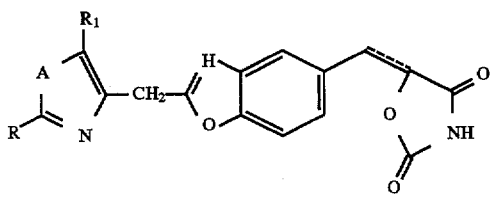

XIII

A still further embodiment of the present invention is the use of pharmaceutical composition for administering an effective amount of a compound of the preceding Formulas I through XIII along with a pharmaceutically acceptable carrier in unit dosage form in the treatment methods mentioned above.

The compounds used in the treatment methods of the invention, which are 5-[4-(chromoanalkoxy)benzyl] thiazolidene derivatives, may be represented by the Formulas (Ia), (Ib), and (Ic)

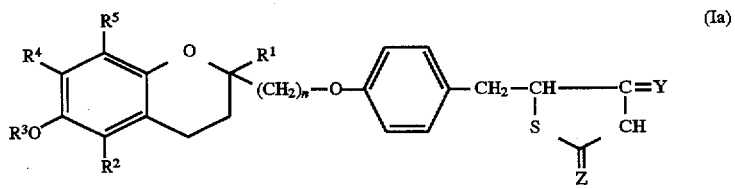
(Ia)

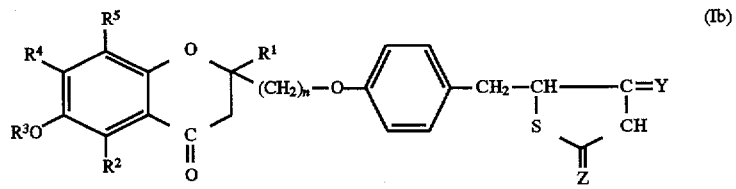
(Ib)

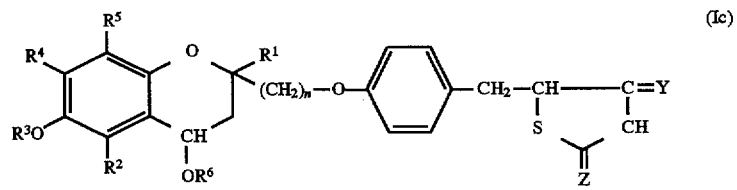
(Ic)

or a pharmaceutically acceptable salt thereof wherein the dotted line represents a bond or no bond; R is cycloalkyl of three to seven carbon atoms, naphthyl, thienyl, furyl, phenyl or substituted phenyl wherein said substituent is alkyl of one to three carbon atoms, alkoxy of one to three carbon atoms, trifluoromethyl, chloro, fluoro or bis(trifluoromethyl); $R_1$ is alkyl of one to three carbon atoms; X is O or C=O; a is O or S; and B is N or CH.

A preferred group of compounds are those of formula XI wherein the dotted line represents no bond, $R_1$ is methyl, X is O and A is O. Especially preferred within this group are the compounds where R is phenyl, 2-naphthyl and 3,5-bis (trifluoromethyl)phenyl.

A second group of preferred compounds are those of formula XII wherein the dotted line represents no bond, $R_1$ is methyl and A is O. Especially preferred within this group are compounds where B is CH and R is phenyl, p-tolyl, m-tolyl, cyclohexyl and 2-naphthyl. Also especially preferred is the compound where B is N and R is phenyl.

(in which $R^1$, $R^2$, $R^3$, $R^4$, $R^5$, $R^6$, n, Y, and Z are as defined above) and include pharmaceutically acceptable salts thereof.

In the compounds of the invention, where $R^1$ or $R^2$ represents an alkyl group, this may be a straight or branched chain alkyl group having from 1 to 5 carbon atoms and is preferably a primary or secondary alkyl group, for example the methyl, ethyl, propyl, isopropyl, butyl, isobutyl, pentyl, or isopentyl group.

Where $R^3$, $R^6$, or $R^{6'}$ represents an aliphatic acyl group, this preferably has from 1 to 6 carbon atoms and may include one or more carbon-carbon double or triple bonds. Examples of such groups include the formyl, acetyl, propionyl, butyryl, isobutyryl, pivaloyl, hexanoyl, acryloyl, methacryloyl, and crotonyl groups.

Where $R^3$, $R^6$, or $R^{6'}$ represents an alicyclic acyl group, it is preferably a cyclopentanecarbonyl, cyclohexanecarbonyl, or cycloheptanecarbonyl group.

Where $R^3$, $R^6$, or $R^{6'}$ represents an aromatic acyl group, the aromatic moiety thereof may optionally have one or more substituents (for example, nitro, amino, alkylamino, dialkylamino, alkoxy, halo, alkyl, or hydroxy substituents); examples of such aromatic acyl groups included the benzoyl, p-nitrobenzoyl, m-fluorobenzoyl, o-chlorobenzoyl, p-aminobenzoyl, m-(dimethylamino)benzoyl, o-methoxybenzoyl, 3,4-dichlorobenzoyl, 3,5-di-t-butyl-4-hydroxybenzoyl, and 1-naphthoyl groups.

Where $R^3$, $R^6$, or $R^{6'}$ represents a heterocyclic acyl group, the heterocyclic moiety thereof preferably has one or more, preferably one, oxygen, sulfur, or nitrogen hetero atoms and has from 4 to 7 ring atoms; examples of such heterocyclic acyl groups include the 2-furoyl, 3-thenoyl, 3-pyridinecarbonyl (nicotinoyl), and 4-pyridinecarbonyl groups.

Where $R^3$, $R^6$, or $R^{6'}$ represents an araliphatic acyl group, the aliphatic moiety thereof may optionally have one or more carbon-carbon double or triple bonds and the aryl moiety thereof may optionally have one or more substituents (for example, nitro, amino, alkylamino, dialkylamino, alkoxy, halo, alkyl, or hydroxy substituents); examples of such araliphatic acyl groups include the phenylacetyl, p-chlorophenylacetyl, phenylpropionyl, and cinnamoyl groups.

Where $R^3$, $R^6$, or $R^{6'}$ represents a ($C_1$–$C_6$ alkoxy) carbonyl group, the alkyl moiety thereof may be any one of those alkyl groups as defined for $R^1$ and $R^2$, but is preferably a methyl or ethyl group, and the alkoxycarbonyl group represented by $R^3$, $R^6$, or $R^{6'}$ is therefore preferably a methoxycarbonyl or ethoxycarbonyl group.

Where $R^3$, $R^6$, or $R^{6'}$ represents an aralkyloxycarbonyl group, the aralkyl moiety thereof may be any one of those included within the araliphatic acyl group represented by $R^3$, $R^6$, or $R^{6'}$, but is preferably a benzyloxycarbonyl group.

Where $R^4$ and $R^5$ represent alkyl groups, they may be the same or different and may be straight or branched chain alkyl groups. They preferably have from 1 to 5 carbon atoms and examples include the methyl, ethyl, propyl, isopropyl, butyl, isobutyl, t-butyl, pentyl, and isopentyl groups.

Where $R^4$ and $R^5$ represent alkoxy groups, these may be the same or different and may be straight or branched chain groups, preferably having from 1 to 4 carbon atoms. Examples include the methoxy, ethoxy, propoxy, isopropoxy, and butoxy groups. Alternatively, $R^4$ and $R^5$ may together represent a $C_1$–$C_4$ alkylenedioxy group, more preferably a methylenedioxy or ethylenedioxy group.

Preferred classes of compounds of Formula I are as follows:

(1) Compounds in which $R^3$ represents a hydrogen atom, a $C_1$–$C_6$ aliphatic acyl group, an aromatic acyl group, or a heterocyclic acyl group.

(2) Compounds in which Y represents an oxygen atom; $R^1$ and $R^2$ are the same or different and each represents a hydrogen atom or a $C_1$–$C_5$ alkyl group; $R^3$ represents a hydrogen atom, a $C_1$–$C_6$ aliphatic acyl group, an aromatic acyl group, or a pyridinecarbonyl group; and $R^4$ and $R^5$ are the same or different and each represents a hydrogen atom, a $C_1$–$C_5$ alkyl group, or a $C_1$ or $C_2$ alkoxy group.

(3) Compounds as defined in (2) above, in which: $R^1$, $R^2$, $R^4$, and $R^5$ are the same or different and each represents a hydrogen atom or a $C_1$–$C_5$ alkyl group; n is 1 or 2; and W represents the —$CH_2$— or >CO group.

(4) Compounds as defined in (3) above, in which $R^3$ represents a hydrogen atom, a $C_1$–$C_5$ aliphatic acyl group, a benzoyl group, or a nicotinyl group.

(5) Compounds as defined in (4) above, in which: $R^1$ and $R^4$ are the same or different and each represents a $C_1$–$C_5$ alkyl group; $R^2$ and $R^5$ are the same or different and each represents the hydrogen atom or the methyl group; and $R^3$ represents a hydrogen atom or a $C_1$–$C_4$ aliphatic acyl group.

(6) Compounds in which: W represents the —$CH_2$— or >CO group; Y and Z both represent oxygen atoms; n is 1 or 2; $R^1$ and $R^4$ are the same or different and each represents a $C_1$–$C_4$ alkyl group; $R^2$ and $R^5$ are the same or different and each represents the hydrogen atom or the methyl group; and $R^3$ represents a hydrogen atom or a $C_1$–$C_4$ aliphatic acyl group.

(7) Compounds as defined in (6) above, in which n is 1.

(8) Compounds as defined in (6) or (7) above, in which W represents the —$CH_2$— group.

Preferred compounds among the compounds of Formula I are those wherein:

$R^1$ is a $C_1$–$C_4$ alkyl group, more preferably a methyl or isobutyl group, most preferably a methyl group;

$R^2$ is a hydrogen atom or a $C_1$–$C_4$ alkyl group, preferably a hydrogen atom, or a methyl or isopropyl group, more preferably a hydrogen atom or a methyl group, most preferably a methyl group;

$R^3$ is a hydrogen atom, a $C_1$–$C_4$ aliphatic acyl group, an aromatic acyl group or a pyridinecarbonyl group, preferably a hydrogen atom, or an acetyl, butyryl, benzoyl, or nicotinyl group, more preferably a hydrogen atom or an acetyl, butyryl or benzoyl group, most preferably a hydrogen atom or an acetyl group;

$R^4$ is a hydrogen atom, a $C_1$–$C_4$ alkyl group or a $C_1$ or $C_2$ alkoxy group, preferably a methyl, isopropyl, t-butyl, or methoxy group, more preferably a methyl or t-butyl group, most preferably a methyl group;

$R^5$ is a hydrogen atom, a $C_1$–$C_4$ alkyl group or a $C_1$ or $C_2$ alkoxy group, preferably a hydrogen atom, or a methyl or methoxy group, more preferably a hydrogen atom or a methyl group, and most preferably a methyl group;

n is 1 or 2, preferably 1;

Y is an oxygen atom;

Z is an oxygen atom or an imino group, most preferably an oxygen atom; and

W is a —$CH_2$— or >C=O group, preferably a —$CH_2$— group.

Referring to the general Formula II, the substituents may be any from 1 to 3 selected from nitro, amino, alkylamino, dialkylamino, alkoxy, halo, alkyl, or hydroxy, the aromatic acyl group may be benzoyl and naphthoyl. The alkyl group $R_{11}$ may be a straight chain or branched alkyl of 1 to 10 carbon atoms, such as methyl, ethyl, n-propyl, i-propyl, n-butyl, i-butyl, t-butyl, n-pentyl, i-pentyl, n-hexyl, n-heptyl, n-octyl, n-nonyl, and n-decyl; the cycloalkyl group $R_{11}$ may be a cycloalkyl group of 3 to 7 carbon atoms, such as cyclopropyl, cyclopentyl, cyclohexyl, and cycloheptyl; and the phenylalkyl group $R_{11}$ may be a phenylalkyl group of 7 to 11 carbon atoms such as benzyl and phenethyl. As examples of the heterocyclic group $R_{11}$ may be mentioned 5- or 6-membered groups each including 1 or 2 hetero-atoms selected from among nitrogen, oxygen, and sulfur, such as pyridyl, thienyl, furyl, thiazolyl, etc. When $R_{11}$ is

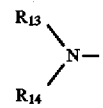

the lower alkyls $R_{13}$ and $R_{14}$ may each be a lower alkyl of 1 to 4 carbon atoms, such as methyl, ethyl, n-propyl, i-propyl, and n-butyl. When $R_{13}$ and $R_{14}$ are combined to each other to form a 5- or 6-membered heterocyclic group as taken together with the adjacent N atom, i.e., in the form of

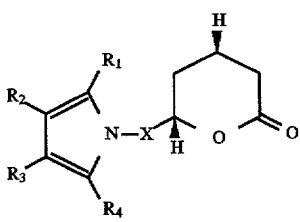

this heterocyclic group may further include a heteroatom selected from among nitrogen, oxygen, and sulfur as exemplified by piperidino, morpholino, pyrrolidino, and piperazino. The lower alkylene group $R_{12}$ may contain 1 to 3 carbon atoms and thus may be, for example, methylene, ethylene, or trimethylene. The bond $R_{12}$ is equivalent to the symbol "-", ".", or the like which is used in chemical structural formulas, and when $R_{12}$ represents such a bond, the compound of general Formula II is represented by the following general Formula II(a)

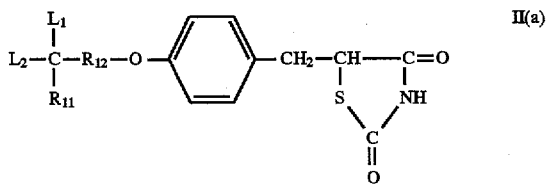

Thus, when $R_{12}$ is a bond, the atoms adjacent thereto on both sides are directly combined together. As examples of the lower alkyls $L_1$ and $L_2$, there may be mentioned lower alkyl groups of 1 to 3 carbon atoms, such as methyl and ethyl. The alkylene group formed as $L_1$ and $L_2$ are joined together is a group of the formula —$(CH_2)_n$— [where n is an integer of 2 to 6]. The cycloalkyl, phenylalkyl, phenyl, and heterocyclic groups mentioned above, as well as said heterocyclic group

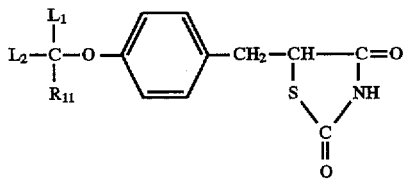

may have 1 to 3 substituents in optional positions on the respective rings. As examples of such substituents may be mentioned lower alkyls (e.g., methyl, ethyl, etc.), lower alkoxy groups (e.g., methoxy, ethoxy, etc.), halogens (e.g., chlorine, bromine, etc.), and hydroxyl. The case also falls within the scope of the general Formula II that an alkylenedioxy group of the formula —O—$(CH_2)_m$—O— [is an integer of 1 to 3], such as methylenedioxy, is attached to the two adjacent carbon atoms on the ring to form an additional ring.

The preferred compounds of Formula III are those wherein $R_{15}$ and $R_{16}$ are independently hydrogen, lower alkyl containing 1 to 6 carbon atoms, alkoxy containing 1 to 6 carbon atoms, halogen, ethynyl, nitrile, trifluoromethyl, vinyl, or nitro; n is 1 or 2 and the pharmaceutically acceptable salts thereof.

Preferred in Formula IV are compounds wherein the dotted line represents no bond, particularly wherein D is CO or CHOH. More preferred are compounds wherein V is —CH═CH—, —CH═N— or S and n is 2, particularly those compounds wherein X is O and Y is N, X is S and Y is N, X is S and Y is CH or X is —CH═N— and Y is CH. In the most preferred compounds X is O or S and Y is N forming an oxazol-4-yl, oxazol-5-yl, thiazol-4-yl, or thiazol-5-yl group; most particularly a 2-[(2-thienyl), (2-furyl), phenyl, or substituted phenyl]-5-methyl-4-oxazolyl group.

The preferred compounds in Formula V are:

a) those wherein the dotted line represents no bond, A and B are each CH, $X_1$ is CO, n is 0, $R_{19}$ is hydrogen, $Z_2$ is $CH_2CH_2$ or CH═CH and $X_3$ is hydrogen, particularly when $X_2$ is hydrogen, 2-methoxy, 4-benzyloxy, or 4-phenyl;

b) those wherein A and B are each CH, $X_1$ is S or $SO_2$, n is 0, $R_{19}$ is hydrogen, $Z_2$ is $CH_2CH_2$ and $X_3$ is hydrogen, particularly when $X_2$ is hydrogen or 4-chloro.

A preferred group of compounds is that of Formula VI wherein $R_{23}$ is ($C_1$–$C_6$)alkyl, ($C_3$–$C_7$)cycloalkyl, phenyl, halophenyl, or ($C_1$–$C_6$)alkylphenyl. Especially preferred within this group are the compounds where $R_{23}$ is phenyl, methylphenyl, fluorophenyl, chlorophenyl, or cyclohexyl.

When used herein with regard to Formulas VII through X, the term "aryl" includes phenyl and naphthyl, suitably phenyl, optionally substituted with up to 5, preferably up to 3, groups selected from halogen, alkyl, phenyl, alkoxy, haloalkyl, hydroxy, amino, nitro, carboxy, alkoxycarbonyl, alkoxycarbonylalkyl, alkylcarbonyloxy, or alkylcarbonyl groups.

The term "halogen" refers to fluorine, chlorine, bromine, and iodine; preferably chlorine.

The terms "alkyl" and "alkoxy" relate to groups having straight or branched carbon chains, containing up to 12 carbon atoms.

Suitable alkyl groups are $C_{1-12}$ alkyl groups, especially $C_{1-6}$ alkyl groups, e.g., methyl, ethyl, n-propyl, iso-propyl, n-butyl, isobutyl, or tert-butyl groups.

Suitable substituents for any alkyl group include those indicated above in relation to the term "aryl".

Suitable substituents for any heterocyclyl group include up to 4 substituents selected from the group consisting of alkyl, alkoxy, aryl, and halogen or any 2 substituents on adjacent carbon atoms, together with the carbon atoms to which they are attached, may form an aryl group, preferably a benzene ring, and wherein the carbon atoms of the aryl group represented by the said 2 substituents may themselves be substituted or unsubstituted.

Specific examples of compounds of the present invention are given in the following list:

(+)-5-[[4-[(3,4-dihydro-6-hydroxy-2,5,7,8-tetramethyl-2H-1-benzopyran-2-yl)methoxy]phenyl]methyl]-2,4-thiazolidinedione: (troglitazone);

4-(2-naphthylmethyl)-1,2,3,5-oxathiadiazole-2-oxide;

5-[4-[2-[N-(benzoxazol-2-yl)-N-methylamino]ethoxy]benzyl]-5-methylthiazolidine-2,4-dione;

5-[4-[2-[2,4-dioxo-5-phenylthiazolidin-3-yl)ethoxy]benzyl]-thiazolidine-2,4-dione;

5-[4-[2-[N-methyl-N-(phenoxycarbonyl)amino]ethoxy]benzyl]-thiazolidine-2,4-dione;

5-[4-(2-phenoxyethoxy)benzyl]thiazolidine-2,4-dione;

5-[4-[2-(4-chlorophenyl)ethylsulfonyl]benzyl]thiazolidine-2,4-dione;

5-[4-[3-(5-methyl-2-phenyloxazol-4-yl)propionyl]benzyl]-thiazolidine-2,4-dione;

5-[4-[(1-methylcyclohexyl)methoxy]benzyl]thiadiazolidine-2,4-dione: (ciglitazone);

5-[[4-(3-hydroxy-1-methylcyclohexyl)methoxy]benzyl]-thiadiazolidine-2,4-dione;

5-[4-[2-(5-methyl-2-phenyloxazol-4-yl)ethoxyl]-benzyl]
thiadizolidione-2,4-dione;

5-[4-[2-(5-ethylpyridin-2-yl)ethoxyl]benzyl]-
thiadiazolidine-2,4-dione: (pioglitazone);

5-[(2-benzyl-2,3-dihydrobenzopyran)-5-ylmethyl]-
thiadiazoline-2,4-dione: (englitazone);

5-[[2-(2-naphthylmethyl)benzoxazol]-5-ylmethyl]-
thiadiazoline-2,4-dione;

5-[4-[2-(3-phenylureido)ethoxyl]benzyl]thiadiazoline-2,
4-dione;

5-[4-[2-[N-(benzoxazol-2-yl)-N-methylamino]ethoxy]-
benzy]thiadiazoline-2,4-dione;

5-[4-[3-(5-methyl-2-phenyloxazol-4-yl)propionyl]-
benzyl]thiadiazoline-2,4-dione;

5-[2-(5-methyl-2-phenyloxazol-4-ylmethyl)benzofuran-
5-ylmethyl]-oxazolidine-2,4-dione;

5-[4-[2-[N-methyl-N-(2-pyridyl)amino]ethoxy]-benzyl]
thiazolidine-2,4-dione; and 5-[4-[2-[N-(benzoxazol-2-yl)-N-methylamino]ethoxy]-
benzyl]-oxazolidine-2,4-dione.

As defined herein, "complications of NIDDM" is referred to as cardiovascular complications or several of the metabolic and circulatory disturbances that are associated with hyperglycemia, e.g., insulin resistance, hyperinsulinemia and/or hyperproinsulinemia, delayed insulin release, dyslipidemia, retinopathy, peripheral neuropathy, nephropathy, and hypertension.

The compounds of Formulas I through XIII are capable of further forming pharmaceutically acceptable base salts.

The compounds of Formulas I through XIII are capable of further forming both pharmaceutically acceptable acid addition and/or base salts. All of these forms are within the scope of the present invention.

Pharmaceutically acceptable acid addition salts of the compounds of Formulas I through XIII include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glucamine (see, for example, Berge S. M., et al., "Pharmaceutical Salts," *Journal of Pharmaceutical Science* 1977;66: 1–19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner or as above. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts," *Journal of Pharmaceutical Science* 1977;66: 1–19).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner or as above. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention. Certain of the compounds of the present invention possess one or more chiral centers and each center may exist in different configurations. The compounds can, therefore, form stereoisomers. Although these are all represented herein by a limited number of molecular formulas, the present invention includes the use of both the individual, isolated isomers and mixtures, including racemates, thereof. Where stereospecific synthesis techniques are employed or optically active compounds are employed as starting materials in the preparation of the compounds, individual isomers may be prepared directly; on the other hand, if a mixture of isomers is prepared, the individual isomers may be obtained by conventional resolution techniques, or the mixture may be used as it is, without resolution.

Furthermore, the thiazolidene or oxazolidene part of the compounds of Formulas I through XIII can exist in the form of tautomeric isomers. All of the tautomers are represented by Formulas I through XIII, and are included in the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use in the treatment of at risk populations having IRNIGT, to prevent or delay the onset of NIDDM and complications arising therefrom, the compounds utilized in the pharmaceutical methods of this invention are administered along with a pharmaceutically acceptable carrier at the initial dosage of about 0.01 mg to about 20 mg per kilogram daily. A daily dose range of about 0.01 mg to about 10 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The compounds of Formulas I through XIII are valuable agents in preventing or delaying the onset of NIDDM in patients with IRNIGT. The following illustrates testing to show that compounds have the disclosed activity, using the preferred compound troglitazone.

EXAMPLE 1

In a blind, randomized, fixed-dose, parallel- group, placebo-controlled, outpatient trial, the effects of the test compound, (+)-5-[[4-[(3,4-dihydro-6-hydroxy-2,5,7,8-tetramethyl-2H-1-benzopyran-2-yl)methoxy]phenyl]methyl]-2,4-thiazolidinedione (troglitazone), was compared with that of a placebo on glucose tolerance and on insulin sensitivity. The trial included a 2-week screening period and a 12-week treatment period. Eighteen patients were randomized to treatment with placebo or 400 mg/day of troglitazone. Oral glucose tolerance tests (OGTT), frequently sampled intravenous glucose tolerance tests (FSIGTT) to assess insulin sensitivity and euglycemic glucose clamp studies were performed before study medication, and after 6 weeks and after 12 weeks of randomized treatment.

Patients included in this study were nondiabetic obese adults nine of whom had IGT and the rest of whom had NGT by the WHO criteria as demonstrated by OGTT (Harris M. I., Hadden W. C., Knowler W. C., Berrett P. H., International Criteria for the Diagnosis of Diabetes and Impaired Glucose Tolerance, *Diabetes Care* 1985;8(6): 562–7).

The OGTT was carried out according to the following procedure:

Test was administered in the morning after a 10- to 14-hour fast. Water, but not coffee, could be consumed during the fast. Patients were required to remain seated during the test. Study medication was omitted on the morning of the test and taken with lunch.

5 ml of venous blood was collected into a serum separation tube for baseline.

1.75-g/kg body weight, up to a maximum of 75 g of glucose was administered orally as a liquid beverage to be consumed over no more than 5 minutes.

5 ml of venous blood was collected into a serum separation tube every 30 minutes up to 2 hours, timing from the start of ingestion of the glucose.

Each blood specimen was allowed to clot for 30 minutes. The specimens were centrifuged until clot and serum were separated by a well-formed polymer barrier. Serum was transferred from each specimen, using separate pipettes for each, into plastic vials and frozen immediately. If centrifuging of specimens was delayed for any reason, specimens were refrigerated and centrifuged as soon as possible.

Frozen specimens were examined for oral glucose tolerance according to the WHO diagnostic criteria.

| Serum Glucose mg/dL (mmol/L) | WHO Diagnostic Criteria | | |
|---|---|---|---|
| | Normal | IGT | Diabetes |
| Fasting | <140 (<7.8) | <140 (<7.8) | ≧140 (≧7.8) |
| 2 hour | <140 (<7.8) | 140–199 (7.8–11.1) | ≧200 (≧11.1) |

In the present study a group of 18 (15M, 3F) nondiabetic obese subjects, 9 of whom had impaired glucose tolerance (IGT), were randomized to treatment in a double-blinded fashion with 12 subjects treated with Troglitazone 200 mg BID and 6 subjects treated with a placebo. Of the 12 subjects treated with Troglitazone for a period of 12 weeks, 7 had impaired glucose tolerance (IGT) and 5 had normal glucose tolerance.

Treatment with Troglitazone led to marked improvement in insulin resistance as measured by the euglycemic glucose clamp test at 40 mU/M$^2$/min (mean glucose disposal rate (GDR) increased from 213±18 to 273±18 mg/M²/min, p<0.002) and at 300 mU/M²/min, p<0.01) as well as by frequently sampled intravenous glucose tolerance tests ($S_I$ increased from 0.71±0.16 to 1.55±0.25, p<0.001). After drug treatment, the glycemic response to oral glucose (area under curve, AUC) decreased by 24.3%, and after meal tolerance tests fell by 16.4%.

In the Troglitazone group, the fasting insulin level was reduced from 110±14 to 57±8 pmol/L, p<0.001, and insulin response (AUC) decreased by 40%, p<0.002 and by 41.2%, p<0.007 to oral glucose or mixed meals, respectively. Fasting glucagon levels were reduced slightly (11.5%) but not significantly in the Troglitazone group. Free fatty acid levels were unchanged. Changes in fasting insulin levels correlated well with changes in GDR (r=0.55, p<0.01) and $S_I$ (r=0.57, p<0.005). $S_{IP}$ is calculated by taking the difference in steady state glucose disposal rates between the two studies (Δ GDR) and dividing it by the differences in the steady state insulin levels during the two glucose clamp tests (Δ insulin).

In the placebo group, all indices of insulin and glucose metabolism were unchanged.

Drug treated subjects showed a reduction in systolic blood pressure of 5±2 mmHG, p<0.02 and in diastolic blood pressure of 4±2 mmHg, p<0.03.

Thus, Troglitazone normalized glucose tolerance, and markedly improved insulin resistance and hyperinsulinemia. Since insulin resistance exists in IRNIGT prior to the development of NIDDM, Troglitazone's efficacy at improving insulin resistance is useful in preventing the progression of IRNIGT to NIDDM.

The following tables show the results of testing for IRNIGT vs. the placebo in which all IGT subjects were excluded.

TABLE 1

Summary of Metabolic Measurements Before and After Administration of Troglitazone or Placebo for Twelve Weeks.

| VARIABLE | TROGLITAZONE n = 5 | | PLACEBO n = 4 | |
|---|---|---|---|---|
| | Pre | Post | Pre | Post |
| Fast Plasma Glucose | 96 | 93 | 96 | 93 |
| Fast Plasma Insulin | 14 | 9 | 20 | 16 |
| GDR 40 | 5.3 | 6.0 | 4.7 | 4.5 |
| GDR 300 | 9.4 | 10.3 | 8.6 | 7.9 |
| $S_i$ | 0.93 | 1.51 | 0.79 | 0.58 |
| $S_{IP}$ | 2.1 | 2.7 | 1.45 | 1.62 |

TABLE 2

Summary of Metabolic Measurements Before and After Administration of Troglitazone or Placebeo for Twelve Weeks.

| VARIABLE | TROGLITAZONE n = 5 | | PLACEBO n = 4 | |
|---|---|---|---|---|
| | Pre | Post | Pre | Post |
| OGTT ins AUC | 71 | 50 | 99 | 102 |
| MTT ins AUC | 58 | 42 | 92 | 95 |
| OGTT glu AUC | 26 | 29 | | |
| MTT glu AUC | 14 | 18 | | |

[all values expressed in arbitrary units]
SUMMARY:
OGTT ins AUC reduction: 30%
MTT ins AUC reduction: 28%

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of treating insulin resistant non-impaired glucose tolerance in order to prevent or delay the onset of noninsulin-dependent diabetes mellitus comprising administering to a host suffering therefrom a therapeutically effective amount of a compound of Formula I:

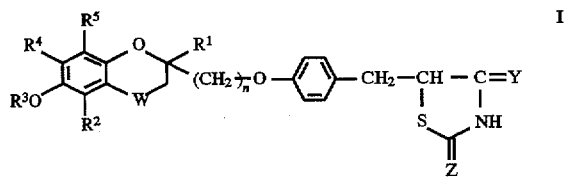

wherein $R^1$ and $R^2$ are the same or different and each represents a hydrogen atom or a $C_1$–$C_5$ alkyl group;

$R^3$ represents a hydrogen atom, a $C_1$–$C_6$ aliphatic acyl group, an alicyclic acyl group, an aromatic acyl group, a heterocyclic acyl group, an araliphatic acyl group, a ($C_1$–$C_6$ alkoxy)carbonyl group, or an aralkyloxycarbonyl group;

$R^4$ and $R^5$ are the same or different and each represents a hydrogen atom, a $C_1$–$C_5$ alkyl group or a $C_1$–$C_5$ alkoxy group, or $R^4$ and $R^5$ together represent a $C_1$–$C_4$ alkylenedioxy group; n is 1, 2, or 3;

W represents the —$CH_2$—, >CO, or CO—$OR^6$ group (in which $R^6$ represents any 1 of the atoms or groups defined for $R^3$ and may be the same as or different from $R^3$); and Y and Z are the same or different and each represents an oxygen atom or an imino (=NH) group;

or a pharmaceutically acceptable salt thereof.

2. The method of claim 1 wherein the compound of formula I is administered in admixture with a pharmaceutically acceptable excipient, diluent, or carrier.

3. The method of claim 2 comprising administering to a host suffering therefrom a therapeutically effective amount of a compound of Formula I wherein Y and Z are oxygen.

4. The method of claim 2 comprising administering to a host suffering therefrom a therapeutically effective amount of a compound of Formula I wherein W is —$CH_2$—.

5. The method of claim 2 comprising administering to a host suffering therefrom a therapeutically effective amount of a compound of Formula I wherein n is 1.

6. The method of claim 2 comprising administering to a host suffering therefrom a therapeutically effective amount of a compound of Formula I wherein $R_1$, $R_2$, $R_4$, and $R_5$ are lower alkyl and $R_3$ is H.

7. The method of claim 2 comprising administering to a host suffering therefrom a therapeutically effective amount of a compound of Formula I wherein Z and Y are oxygen, n is 1, and W is —$CH_2$—.

8. The method of claim 2 comprising administering to a host suffering therefrom a therapeutically effective amount of a compound of Formula I wherein the compound is (+)-5-[[4-[(3,4-dihydro-6-hydroxy-2,5,7,8-tetramethyl-2H-1-benxopyran-2-yl)methoxy]phenyl]methyl]-2,4-thiazolidinedione.

9. A method of treating insulin resistant non-impaired glucose tolerance to prevent or delay the onset of noninsulin-dependent diabetes mellitus comprising administering to a host suffering therefrom a therapeutically effective amount of a compound of Formula II:

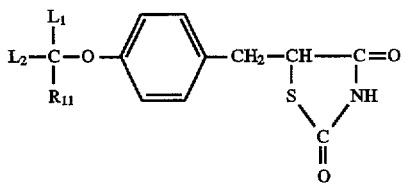

wherein $R_{11}$ is substituted or unsubstituted alkyl, alkoxy, cycloalkyl, phenylalkyl, phenyl, aromatic acyl group, a 5- or 6-membered heterocyclic group including 1 or 2 heteroatoms selected from the group consisting of nitrogen, oxygen, and sulfur, or a group of the formula

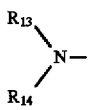

wherein $R_{13}$ and $R_{14}$ are the same or different and each is lower alkyl or $R_{13}$ and $R_{14}$ are combined to each other either directly or as interrupted by a heteroatom selected from the group consisting of nitrogen, oxygen, and sulfur to form a 5- or 6-membered ring;
wherein $R_{12}$ means a bond or a lower alkylene group; and wherein $L_1$ and $L_2$ are the same or different and each is hydrogen or lower alkyl or $L_1$ and $L_2$ are combined to form an alkylene group, or a pharmaceutically acceptable salt thereof.

10. The method of claim 9 wherein the compound of formula II is administered in admixture with a pharmaceutically acceptable excipient, diluent, or carrier.

11. The method of claim 10 comprising administering to a host suffering therefrom a therapeutically effective amount of a compound of Formula II wherein the compound is pioglitazone.

12. The method of claim 10 comprising administering to a host suffering therefrom a therapeutically effective amount of a compound of Formula II wherein the compound is ciglitazone.

13. A method of treating insulin resistant non-impaired glucose tolerance to prevent or delay the onset of noninsulin-dependent diabetes mellitus comprising administering to a host suffering therefrom a therapeutically effective amount of a compound of Formula III:

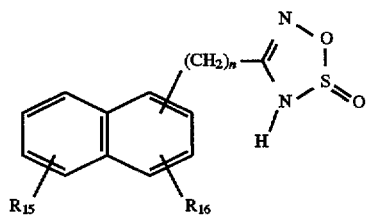

wherein $R_{15}$ and $R_{16}$ are independently hydrogen, lower alkyl containing 1 to 6 carbon atoms, alkoxy containing 1 to 6 carbon atoms, halogen, ethynyl, nitrile, methylthio, trifluoromethyl, vinyl, nitro, or halogen substituted benzyloxy; n is 0 to 4 or a pharmaceutically acceptable salt thereof.

14. A method of treating insulin resistant non-impaired glucose tolerance to prevent or delay the onset of noninsulin-dependent diabetes mellitus comprising administering to a host suffering therefrom a therapeutically effective amount of a compound of Formula IV:

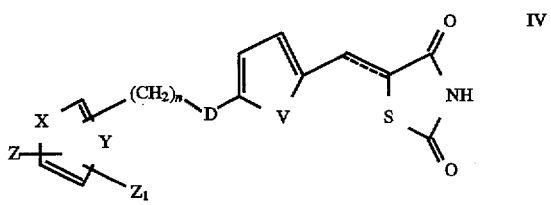

wherein the dotted line represents a bond or no bond;
V is —CH=CH—, —N=CH—, —CH=N— or S;
D is $CH_2$, CHOH, CO, C=NOR$_{17}$ or CH=CH;
X is S, O, NR$_{18}$, —CH=N or —N=CH;
Y is CH or N;
Z is hydrogen, ($C_1$-$C_7$) alkyl, ($C_3$-$C_7$)cycloalkyl, phenyl, naphthyl, pyridyl, furyl, thienyl, or phenyl mono- or disubstituted with the same or different groups which are ($C_1$-$C_3$)alkyl, trifluoromethyl, ($C_1$-$C_3$)alkoxy, fluoro, chloro, or bromo;
Z' is hydrogen or ($C_1$-$C_3$)alkyl;
$R_{17}$ and $R_{18}$ are each independently hydrogen or methyl; and n is 1, 2, or 3;
a pharmaceutically acceptable cationic salt thereof; or a pharmaceutically acceptable acid addition salt thereof when the compound contains a basic nitrogen.

15. A method of treating insulin resistant non-impaired glucose tolerance to prevent or delay the onset of noninsulin-dependent diabetes mellitus comprising administering to a host suffering therefrom a therapeutically effective amount of a compound of Formula V:

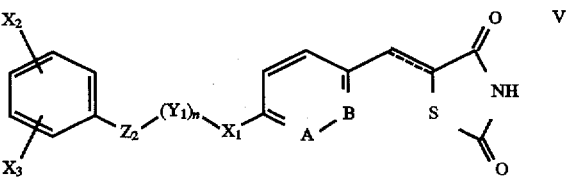

wherein the dotted line represents a bond or no bond;
A and B are each independently CH or N, with the proviso that when A or B is N, the other is CH;
$X_1$ is S, SO, $SO_2$, $CH_2$, CHOH, or CO;
n is 0 or 1;
$Y_1$ is CHR$_{20}$ or R$_{21}$, with the proviso that when n is 1 and $Y_1$ is NR$_{21}$, $X_1$ is $SO_2$ or CO;
$Z_2$ is CHR$_{22}$, $CH_2CH_2$, CH=CH,

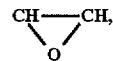

$OCH_2$, $SCH_2$, $SOCH_2$ or $SO_2CH_2$;
$R_{19}$, $R_{20}$, $R_{21}$, and $R_{22}$ are each independently hydrogen or methyl; and
$X_2$ and $X_3$ are each independently hydrogen, methyl, trifluoromethyl, phenyl, benzyl, hydroxy, methoxy, phenoxy, benzyloxy, bromo, chloro, or fluoro;
a pharmaceutically acceptable cationic salt thereof; or
a pharmaceutically acceptable acid addition salt thereof when A or B is N.

16. A method of treating insulin resistant non-impaired glucose tolerance to prevent or delay the onset of noninsulin-dependent diabetes mellitus comprising administering to a host suffering therefrom a therapeutically effective amount of a compound of Formula VI:

$$\text{Formula VI}$$

or a pharmaceutically acceptable salt thereof wherein $R_{23}$ is alkyl of 1 to 6 carbon atoms, cycloalkyl of 3 to 7 carbon atoms, phenyl, or mono- or disubstituted phenyl wherein said substituents are independently alkyl of 1 to 6 carbon atoms, alkoxy of 1 to 3 carbon atoms, halogen, or trifluoromethyl.

17. A method of treating insulin resistant non-impaired glucose tolerance to prevent or delay the onset of noninsulin-dependent diabetes mellitus comprising administering to a host suffering therefrom a therapeutically effective amount of a compound of Formula VII:

$$A_2-O-CO-N(R_{24})-(CH_2)_n-X_4-(A_3)-CH(R_{25})(R_{26})-C(=O)-NH-... \quad \text{VII}$$

or a tautomeric form thereof and/or a pharmaceutically acceptable salt thereof, and/or a pharmaceutically acceptable solvate thereof, wherein:

- $A_2$ represents an alkyl group, a substituted or unsubstituted aryl group, or an aralkyl group wherein the alkylene or the aryl moiety may be substituted or unsubstituted;
- $A_3$ represents a benzene ring having in total up to 3 optional substituents;
- $R_{24}$ represents a hydrogen atom, an alkyl group, an acyl group, an aralkyl group wherein the alkyl, or the aryl moiety may be substituted or unsubstituted, or a substituted or unsubstituted aryl group; or $A_2$ together with $R_{24}$ represents substituted or unsubstituted $C_{2-3}$ polymethylene group, optional substituents for the polymethylene group being selected from alkyl or aryl or adjacent substituents together with the methylene carbon atoms to which they are attached form a substituted or unsubstituted phenylene group;
- $R_{25}$ and $R_{26}$ each represent hydrogen, or $R_{25}$ and $R_{26}$ together represent a bond;
- $X_4$ represents O or S; and
- n represents an integer in the range of from 2 to 6.

18. A method of treating insulin resistant non-impaired glucose tolerance to prevent or delay the onset of noninsulin-dependent diabetes mellitus comprising administering to a host suffering therefrom a therapeutically effective amount of a compound of Formula VIII in unit dosage form $$\text{Formula VIII}$$

or a tautomeric form thereof and/or a pharmaceutically acceptable salt thereof, and/or a pharmaceutically acceptable solvate therefor, wherein:

- $R_{27}$ and $R_{28}$ each independently represent an alkyl group, a substituted or unsubstituted aryl group, or an aralkyl group being substituted or unsubstituted in the aryl or alkyl moiety;
- or $R_{27}$ together with $R_{28}$ represents a linking group, the linking group consisting of an optionally substituted methylene group and either a further optionally substituted methylene group or an O or S atom, optional substituents for the said methylene groups being selected from alkyl-, aryl, or aralkyl, or substituents of adjacent methylene groups together with the carbon atoms to which they are attached form a substituted or unsubstituted phenylene group;
- $R_{29}$ and $R_{30}$ each represent hydrogen, or $R_{29}$ and $R_{30}$ together represent a bond;
- $A_4$ represents a benzene ring having in total up to 3 optional substituents;
- $X_5$ represents O or S; and
- n represents an integer in the range of from 2 to 6.

19. A method of treating insulin resistant non-impaired glucose tolerance to prevent or delay the onset of noninsulin-dependent diabetes mellitus comprising administering to a host suffering therefrom a therapeutically effective amount of a compound of Formula IX:

$$A_5-X_6-(CH_2)_n-Y_2-(A_6)-CH_2-C(R_{31})(=O)-NH-... \quad \text{IX}$$

or a tautomeric form thereof and/or a pharmaceutically acceptable salt thereof, and/or a pharmaceutically acceptable solvate thereof, wherein:

- $A_5$ represents a substituted or unsubstituted aromatic heterocyclyl group;
- $A_6$ represents a benzene ring having in total up to 5 substituents;
- $X_6$ represents O, S, or $NR_{32}$ wherein $R_{32}$ represents a hydrogen atom, an alkyl group, an acyl group, an aralkyl group, wherein the aryl moiety may be substituted or unsubstituted, or a substituted or unsubstituted aryl group;
- $Y_2$ represents O or S;
- $R_{31}$ represents an alkyl, aralkyl, or aryl group; and
- n represents an integer in the range of from 2 to 6.

20. A method of treating insulin resistant non-impaired glucose tolerance to prevent or delay the onset of noninsulin-dependent diabetes mellitus comprising administering to a host suffering therefrom a therapeutically effective amount of a compound of Formula X:

$$A_7-X_8-(CH_2)_n-Y_3-(A_8)-CH(R_{37})(R_{38})-C(=O)-NH-... \quad \text{X}$$

or a tautomeric form thereof and/or a pharmaceutically acceptable salt thereof, and/or a pharmaceutically acceptable solvate thereof, wherein:

- $A_7$ represents a substituted or unsubstituted aryl group;
- $A_8$ represents a benzene ring having in total up to 5 substituents;

$X_8$ represents O, S, or $NR_{39}$ wherein $R_{39}$ represents a hydrogen atom, an alkyl group, an acyl group, an aralkyl group, wherein the aryl moiety may be substituted or unsubstituted, or a substituted or unsubstituted aryl group;

$Y_3$ represents O or S;

$R_{37}$ represents hydrogen;

$R_{38}$ represents hydrogen or an alkyl, aralkyl, or aryl group or $R_{37}$ together with $R_{38}$ represents a bond; and n represents an integer in the range of from 2 to 6.

21. A method of treating insulin resistant non-impaired glucose tolerance to prevent or delay the onset of noninsulin-dependent diabetes mellitus comprising administering to a host suffering therefrom a therapeutically effective amount of a compound of Formula XI:

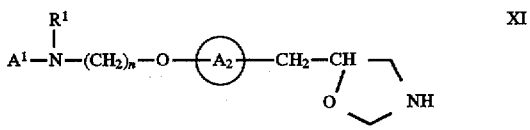

or a tautomeric form thereof and/or a pharmaceutically acceptable salt thereof, and/or a pharmaceutically acceptable solvate thereof, wherein:

$A^1$ represents a substituted or unsubstituted aromatic heterocyclyl group;

$R^1$ represents a hydrogen atom, an alkyl group, an acyl group, an aralkyl group, wherein the aryl moiety may be substituted or unsubstituted, or a substituted or unsubstituted aryl group;

$A^2$ represents a benzene ring having in total up to five substituents; and n represents an integer in the range of from 2 to 6.

22. A method of treating insulin resistant non-impaired glucose tolerance to prevent or delay the onset of noninsulin-dependent diabetes mellitus comprising administering to a host suffering therefrom a therapeutically effective amount of a compound of Formula XII or XIII:

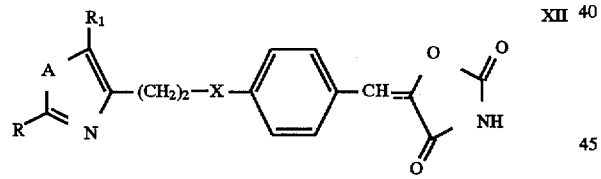

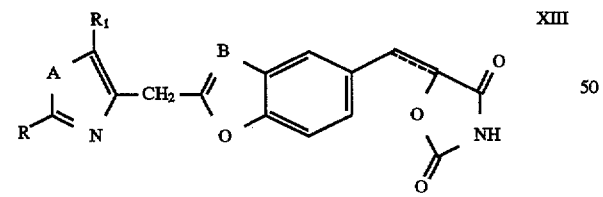

or a pharmaceutically acceptable salt thereof wherein the dotted line represents a bond or no bond; R is cycloalkyl of three to seven carbon atoms, naphthyl, thienyl, furyl, phenyl or substituted phenyl wherein said substituent is alkyl of one to three carbon atoms, alkoxy of one to three carbon atoms, trifluoromethyl, chloro, fluoro or bis(trifluoromethyl); $R_1$ is alkyl of one to three carbon atoms; X is O or C=O; A is O or S; and B is N or CH.

23. A method of treating insulin resistant non-impaired glucose tolerance to prevent or delay the onset of noninsulin-dependent diabetes mellitus comprising administering to a host suffering therefrom a therapeutically effective amount of a compound selected from the group consisting of 4-(2-naphthylmethyl)-1,2,3,5-oxathiadiazole-2-oxide;

5-[4-[2-[N-(benzoxazol-2-yl)-N-methylamino]ethoxy]benzyl]-5-methylthiazolidine-2,4-dione;

5-[4-[2-[2,4-dioxo-5-phenylthiazolidin-3-yl)ethoxy]benzyl]-thiazolidine-2,4-dione;

5-[4-[2-[N-methyl-N-(phenoxycarbonyl)amino]ethoxy]benzyl]-thiazolidine-2,4-dione;

5-[4-(2-phenoxyethoxy)benzyl]thiazolidine-2,4-dione;

5-[4-[2-(4-chlorophenyl)ethylsulfonyl]benzyl]thiazolidine-2,4-dione;

5-[4-[3-(5-methyl-2-phenyloxazol-4-yl)propionyl]benzyl]-thiazolidine-2,4-dione;

5-[4-[(1-methylcyclohexyl)methoxy]benzyl]thiadiazolidine-2,4-dione: (ciglitazone);

5-[[4-(3-hydroxy-1-methylcyclohexyl)methoxy]benzyl]-thiadiazolidine-2,4-dione;

5-[4-[2-(5-methyl-2-phenyloxazol-4-yl)ethoxyl]-benzyl]thiadizolidione-2,4-dione;

5-[4-[2-(5-ethylpyridin-2-yl)ethoxyl]benzyl]-thiadiazolidine-2,4-dione: (pioglitazone);

5-[(2-benzyl-2,3-dihydrobenzopyran)-5-ylmethyl]-thiadiazoline-2,4-dione: (englitazone);

5-[[2-(2-naphthylmethyl)benzoxazol]-5-ylmethyl]-thiadiazoline-2,4-dione;

5-[4-[2-(3-phenylureido)ethoxyl]benzyl]thiadiazoline-2,4-dione;

5-[4-[2-[N-(benzoxazol-2-yl)-N-methylamino]ethoxy]-benzy]thiadiazoline-2,4-dione;

5-[4-[3-(5-methyl-2-phenyloxazol-4-yl)propionyl]-benzyl]thiadiazoline-2,4-dione;

5-[2-(5-methyl-2-phenyloxazol-4-ylmethyl)benzofuran-5-ylmethyl-oxazolidine-2,4-dione; and 5-[4-[2-[N-(benzoxazol-2-yl)-N-methylamino]ethoxy]-benzyl]-oxazolidine-2,4-dione.

24. The method of claim 6 comprising administering to a host suffering therefrom a therapeutically effective amount of a compound of Formula I wherein Z and Y are oxygen, n is 1, and W is —$CH_2$—.

25. A method of treating insulin resistant non-impaired glucose tolerance to prevent or delay the onset of noninsulin-dependent diabetes mellitus comprising administering to a host suffering therefrom a therapeutically effective amount of troglitazone.

26. A method of treating insulin resistant non-impaired glucose tolerance to prevent or delay the onset of noninsulin-dependent diabetes mellitus comprising administering to a host suffering therefrom a therapeutically effective amount of 5-[4-[2-[N-methyl-N-(2-pyridyl)amino]ethoxy]-benzyl]thiazolidine-2,4-dione.

* * * * *